United States Patent [19]
Hirai et al.

[11] Patent Number: 4,704,522
[45] Date of Patent: Nov. 3, 1987

[54] TWO DIMENSIONAL WEAK EMITTED LIGHT MEASURING DEVICE

[75] Inventors: Nobuyuki Hirai; Mitsuo Watanabe, both of Shizuoka, Japan

[73] Assignee: Hamamatsu Photonics Kabushiki Kaisha, Shizuoka, Japan

[21] Appl. No.: 865,124

[22] Filed: May 20, 1986

[30] Foreign Application Priority Data

May 21, 1985 [JP] Japan .................... 60-108740

[51] Int. Cl.$^4$ ............................ H01J 31/50
[52] U.S. Cl. .................. 250/213 VT; 364/414
[58] Field of Search .............. 250/213 R, 213 VT; 364/414

[56] References Cited

U.S. PATENT DOCUMENTS 4,461,572 7/1984 Tsuchiya .................. 250/213 VT
4,611,920 9/1986 Tsuchiya .................. 250/213 VT
4,645,918 2/1987 Tsuchiya et al. ........... 250/213 VT

FOREIGN PATENT DOCUMENTS 2126043A 6/1983 United Kingdom .

Primary Examiner—Edward P. Westin
Assistant Examiner—Jessica L. Ruoff
Attorney, Agent, or Firm—Finnegan, Henderson, Farabow, Garrett, and Dunner

[57] ABSTRACT

A two dimensional weak emitted light measuring device for determining and indicating the intensity and location of single photon light emitted from a specimen excited by radiation. The device includes an incident position detecting tube and a calculating unit for generating coordinates of the incident radiation and a data processing unit for producing specimen identification data in response to the coordinates and timing signals.

6 Claims, 3 Drawing Figures

4,704,522

TWO DIMENSIONAL WEAK EMITTED LIGHT MEASURING DEVICE

FIELD OF THE INVENTION

This invention relates to a two-dimensional weak emitted light measuring device that is capable of measuring weak light emitted by a wide specimen together with data on the position of the light emission.

BACKGROUND OF THE INVENTION

In order to measure a single photon level light emission phenomenon in the range of subnanoseconds, a measuring device with a photomultiplier according to a single photon counting method has been employed in the art.

FIG. 3 is a schematic diagram showing a conventional device for measuring a light emission phenomenon according to a single photon level counting method. In FIG. 3, specimen 1 is a vegetable photosynthesis coloring matter. The specimen 1 is repeatedly excited by the exciting light 2 which is a laser pulse train having a pulse width of the order to 10 p sec. A part of the exciting light 2 is received by a photo-diode 3 so that it is converted into an electrical signal.

The electrical signal is amplified by an amplifier 8 and subjected to waveform shaping by a constant fraction discriminator 12, to provide a reference signal pulse. The jitter of the reference signal pulse is of the order of 10 p sec.

On the other hand, a single photon level fluorescent light emitted by the specimen 1 that is excited by the exciting light 2 is applied through an optical system 6 to a photomultiplier 30. The fluorescent light is detected by the photomultiplier 30 and amplified by an amplifier 7. The output of the amplifier 7 is applied to a constant fraction discriminator 11, to form a pulse whose jitter is of the order of 200 p sec. The pulse is applied to a time-to-pulse height converter 14. On the other hand, the aforementioned reference signal pulse is sufficiently delayed by a delay circuit 12a so that the time difference between the pulse outputted by the constant fraction discriminator 11 and the reference signal pulse is smaller than the full scale of the time-to-pulse height converter 14. The pulse thus delayed is also applied to the time-to-pulse height converter 14, so that a voltage corresponding to the time difference between those pulses is outputted. The voltage thus outputted is applied to a pulse height analyzer 31.

In the pulse height analyzer 31, the voltage corresponding to the time difference is quantized, and the output is accumulated a plurality of times for each quantizing position. A graph is formed by plotting the time intervals on the horizontal axis and the degrees obtained through a number of exciting operations on the vertical axis. In this case, the light emission time characteristic of the specimen 1 excited by the exciting light 2 can be measured with a time resolution of the order of 200 p sec.

It can be considered that all the parts of a specimen do not emit the same weak light beams having the same attenuation waveforms. Therefore, when the above-described measuring device is used to measure the weak light beams of all the parts of a wide specimen, it is necessary to perform the above-described measurement for each of the parts on the premise that the specimen is maintained unchanged in characteristic. This is not a valid assumption and leads to inaccurate results.

Another type of photon imaging device that has a micro-channel plate electron multiplier is described in U.K. patent application GB 2 126 043A published on Mar. 14, 1984, and assigned to the present assignee.

OBJECTS AND SUMMARY OF THE INVENTION

An object of the present invention is to provide a device for accurately measuring weak light beams emitted from all portions of a specimen.

Another object of the present invention is to provide a device for the two-dimentional measurement of weak light emitted by a two-dimmensional object.

A further object of the present invention is to provide a device for measuring weak light emitted by a two-dimensional object together with positional data with a time resolution of 200 p sec. or less.

The foregoing and other objects of the present invention are achieved by a two-dimensional weak emitted light measuring device comprising a two-dimensional incident position detecting tube for outputting single photon level incident position data of an image of a specimen that is excited to emit weak light, a reference time pulse generating unit for generating a reference time pulse in synchronization with the excitation, an incident position calculating unit for calculating the output of the two-dimensional incident position detecting tube to output incident position coordinates, a time difference signal generating unit for obtaining the time difference between the time instant when the output of the incident position detecting tube corresponding to the coordinates is produced and the time instant when the reference time pulse is produced to produce a time difference signal in correspondence to the time difference thus obtained, and a data processing unit for integrating the coordinates and the output produced for each time difference for each of a number of excitations.

BRIEF DESCRIPTION OF THE DRAWINGS

The manner by which the above objects and other objects, features, and advantages of the present invention are attained will become more apparent from the following detailed description when it is considered in view of the drawings, wherein.

DETAILED DESCRIPTION OF THE THE PREFERRED EMBODIMENT

Figure 1:
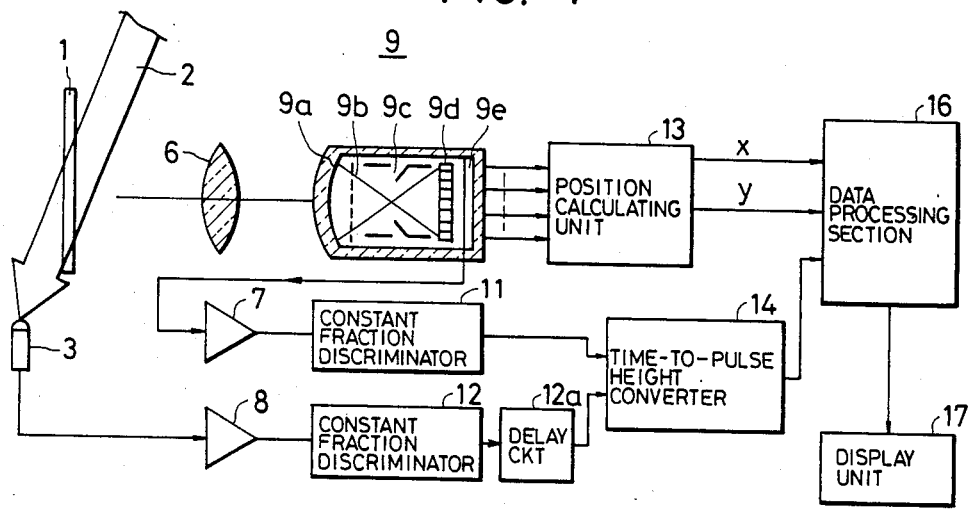
FIG. 1 is a block diagram showing an example of a two-dimensional weak emitted light measuring device according to the present invention.

FIG. 1 is a block diagram showing one example of a two-dimensional weak emitted light measuring device according to the present invention.

As shown in FIG. 1, a specimen 1 is repeatedly excited by the exciting light 2 which lasts for an extremely short period of picoseconds. The exciting light 2 is received by a high-speed photo-diode 3 having a rise time of 50 p sec., amplified by an amplifier 8, and subjected to waveform shaping by a constant fraction discriminator 12, to form a reference signal pulse whose jitter is 10 p sec. or less.

On the other hand, a fluorescent image having an intensity of a single photon level is formed by the materials distributed in the specimen 1. The fluorescent image is applied through an optical system 6 to a two-dimensional incident position detecting tube 9. The tube 9 comprises a photo-electric surface 9a, an accelerating mesh electrode 9b, an electron lens system 9c, a micro channel plate 9d, and a semiconductor incident position detecting unit 9e.

Data on the incident position of the fluorescent light of a single photon level is provided at the output terminal of the semiconductor incident position detecting unit 9e. Data on the incident time is outputted through the electrode of the micro channel plate 9d. The data on the incident time instant is amplified by an amplifier 7. The output of the amplifier 7 is applied to a constant fraction discriminator 11, where it is subjected to waveform shaping. The output of the constant fraction discriminator 11 is applied to a time-to-pulse height converter 14.

The output of the constant fraction discriminator 12, which includes the data concerning the incident time, is delayed by a delay circuit 12a so that the time difference between the output and the aforementioned reference signal pulse is smaller than the full scale of the time-to-pulse height converter 14. The output thus delayed is also applied to the time-to-pulse height converter 14. As a result, the converter 14 outputs a voltage corresponding to the time difference between the pulses.

The output of the semiconductor incident position detecting unit 9e of the incident position detecting tube 9 is applied to a position calculating unit 13, so that the incident position (x, y) is calculated and outputted.

The two-dimensional position signal and the time signal are applied to a data processing section 16, where they are stored. The data processing section 16 integrates the above-described single photon detection data several times.

The above-described position data is divided into $3 \times 3$ picture element units, and the number of times of inputting of a single photon at each picture unit is integrated per unitary time quantized. In this case, data on the variation with time of the weak emitted light of the specimen which corresponds to each of the $3 \times 3$ picture element units can be obtained.

Figure 2:
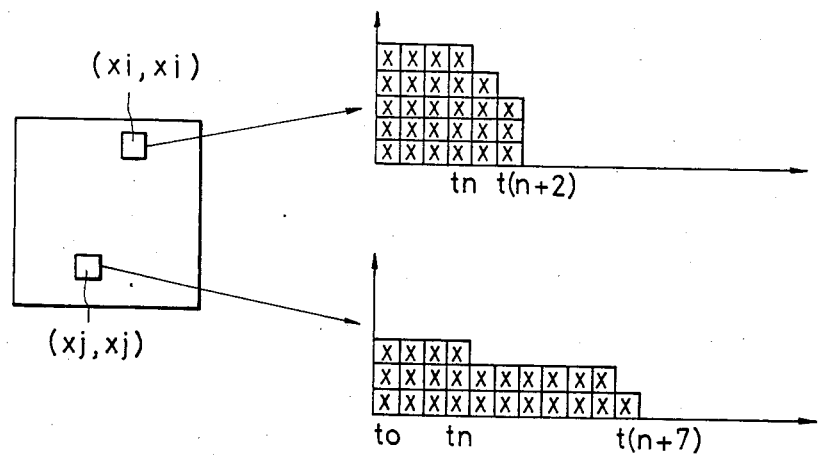
FIG. 2 is an explanatory diagram for a discription of the operating princple of the device of FIG. 1.
Figure 3:
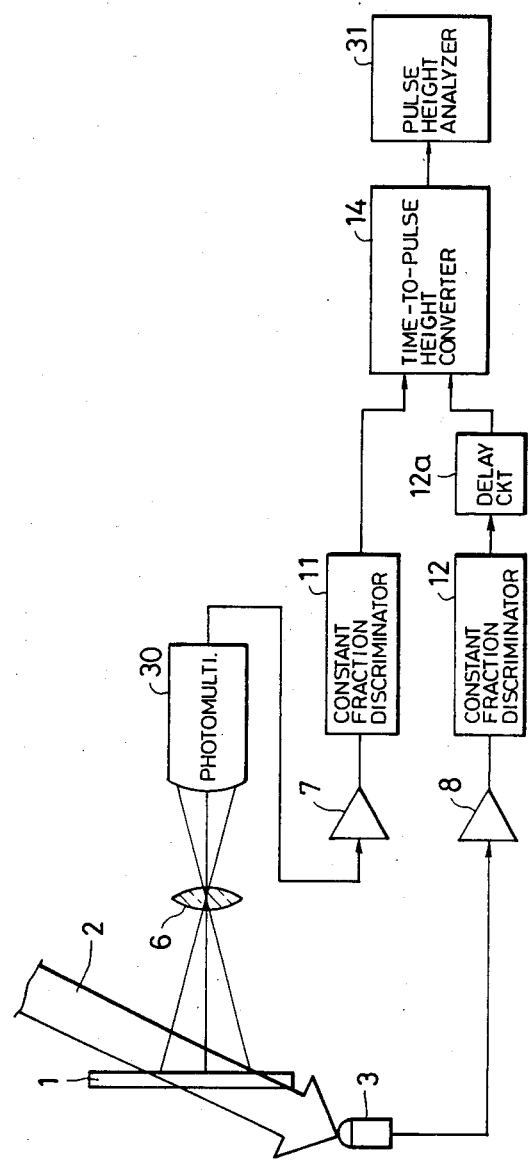
FIG. 3 is a block diagram of a conventional device for measuring light emission phenomena according to a single photon counting method that uses a photomultiplier.

FIG. 2 is a graphical representation showing examples of the above-described data processed by the data processing section 16. More specifically, FIG. 2 shows picture element (xi, yi), eight picture elements immediately adjacent to the picture element (xi, yi) of a two-dimensional picture, and the variation with time of the fluorescent light emission of nine picture elements including a picture element (xj, yj).

In the case of the nine picture elements including the picture element (xi, yi), the measurement is carried out a number of times, and light incidence is effected five times at the quantizied time instant tn after the production of the reference pulse, three times at the time instant t(n+2), and no light incidence is effected after the time instant t(n+2). In the case of the nine picture elements including the picture element (xj, yj), the measurement is carried out a number of times. Light incidence is effected three times at the quantized time instant tn after the production of the reference pulse and twice at the time instant t(n+2), and no light incidence is effected after the time instant t(n+7).

It is considered that different fluorescent materials have different fluorescence attenuation times.

When, in the case where various fluorescent materials are dispersed on the surface of the specimen 1, it is required to detect the position of the material which emits fluorescent light for a certain period of time, for instance in the order of subnanoseconds, the distribution of the material can be detected according to a method in which, of all the data of the picture, that which provides an output only in the range of subnanoseconds is displayed on a display unit 17.

Sometimes, in the two-dimensional incident position detecting tube 9, the electron lens causes time delay radially of the center of the effective picture at the time of detection of photons. However, this can be corrected by the data processing section 16 with distance between the measurement position and the center as a parameter.

As was described above, in the two-dimensional weak emitted light measuring device according to the present invention, the reference time pulse is generated in synchronization with the excitation of fluorescence, and with the aid of the two-dimensional incident position detecting tube the weak emitted light incident position data and the time data from the production of the reference time pulse are outputted and processed, whereby the fluorescence attenuation time including the two-dimensional position data can be measured.

In the case where fluorescent materials are dispersed two-dimensionally in the specimen, for instance, the position of the material that emits fluorescent light only in the range of subnanoseconds can be detected from the data provided by the above-described measurement.

Furthermore, the types of material can be identified from the fluorescene attenuation time thus measured.

It should be understood that the present invention is not limited to the particular embodiment described, but is susceptible to modifications, alterations, and equivalent arrangments within the scope of the appended claims.

What is claimed is:

1. A two-dimensional weak emitted light measuring device comprising:
   a two-dimensional incident position detecting tube for outputting single photon level incident position data responsive to an image of a specimen excited to emit weak light;
   a reference time pulse generating unit for generating a reference time pulse in synchronization with the excitation of the specimen;
   an incident position calculating unit for calculating photon incident position coordinates from the output of said two-dimensional incident position detecting tube;
   a time difference signal generating unit for producing a time difference signal corresponding to the difference between the time instant when said position detecting tube outputs incident position data corresponding to photon incident position coordinates and the time instant when said pulse generating unit generates a reference time pulse; and
   a data processing unit for integrating said incident position coordinates and said output provided for each time difference signal for a plurality of excitations of the specimen to produce measurement data indicating the composition of the specimen.

2. The measuring device according to claim 1, wherein said reference time pulse generating unit includes a high-speed photo-diode for detecting the excitation of the specimen and for producing a reference time in response thereto.

3. The device according to claim 1, wherein said two-dimensional incident position detecting tube comprises:
- a photo-electric surface for receiving said image of the specimen and for generating electrons corresponding to a single photon level in response thereto;
- an accelerating mesh electrode; and
- a semiconductor incident position detecting unit for receiving said electrons and for outputting incident position data corresponding to the incident position of the single photon level light on said photo-electric surface.

4. The device according to claim 3, wherein said two-dimensional incident position detecting tube further includes a micro channel plate between said mesh electrode and said incident position detecting unit for multiplying electrons produced by said photo-electric surface.

5. The device according to claim 1, wherein said incident position calculating unit is adapted to calculate and output said incident position coordinates in response to the output of said semiconductor incident position detecting unit.

6. The device according to claim 1, wherein said time difference signal generating unit includes a time-to-pulse height converter for producing said time difference signal.

* * * * *